(12) United States Patent
Steiner

(10) Patent No.: US 8,158,685 B2
(45) Date of Patent: Apr. 17, 2012

(54) METHOD FOR BONE GROWTH

(76) Inventor: Gregory Gene Steiner, Kopolei, HI (US)

(*) Notice: Subject to any disclaimer, the term of this patent is extended or adjusted under 35 U.S.C. 154(b) by 37 days.

(21) Appl. No.: 11/167,739

(22) Filed: Jun. 25, 2005

(65) Prior Publication Data

US 2006/0008502 A1 Jan. 12, 2006

Related U.S. Application Data

(60) Provisional application No. 60/585,486, filed on Jul. 2, 2004, provisional application No. 60/585,487, filed on Jul. 2, 2004, provisional application No. 60/585,488, filed on Jul. 2, 2004.

(51) Int. Cl.
*A61K 31/015* (2006.01)
(52) U.S. Cl. ........................ 514/764; 514/765
(58) Field of Classification Search ............... 424/49, 424/52, 673, 676, 680, 686, 715, 717; 514/167, 514/474, 684, 764, 765
See application file for complete search history.

(56) References Cited

U.S. PATENT DOCUMENTS

| | | | | |
|---|---|---|---|---|
| 3,287,219 A | * | 11/1966 | Nemanick | 424/676 |
| 5,759,586 A | * | 6/1998 | Fuchs et al. | 424/686 |
| 6,190,695 B1 | * | 2/2001 | Hoshino et al. | 424/464 |
| 6,881,419 B2 | * | 4/2005 | Lovett | 424/439 |

OTHER PUBLICATIONS

Pak et al., "Safe and effective treatment of osteoporosis with intermittent slow release sodium fluoride: augmentation of vertebral bone mass and inhibition of fractures", Journal of Clinical Endocrinology & Metabolism, vol. 68, pp. 150-159 (1989), see the enclosed abstract.*

Matsunaga et al., "The Effect of Vitamin K and D Supplementation on Ovariectomy-Induced Bone Loss", Calcified Tissue International, vol. 65, No. 4, pp. 285-289 (1999), see the enclosed abstract.*

* cited by examiner

*Primary Examiner* — Kevin E Weddington
(74) *Attorney, Agent, or Firm* — Craig M. Stainbrook; Stainbrook & Stainbrook, LLP

(57) ABSTRACT

The present invention relates to novel chemical compositions and methods of treating and regenerating bone in a patient in need thereof. This invention presents a novel chemical composition of matter that stimulates osteoblast formation and inhibits osteoclastic and phagocytosis activity thereby resulting in a significant increase in bone formation.

10 Claims, No Drawings

METHOD FOR BONE GROWTH

The application claims the benefit of U.S. Provisional Application Nos. 60/585,486 and 60/585,487 and 60/585,488 filed on Jul. 2, 2004. The entire teachings of the above applications are incorporated herein.

FIELD OF THE INVENTION

Bone graft surgery is a very common procedure in medicine and dentistry. Bone grafts are used to fill bony defects caused by trauma or disease. Also, bone grafts are used to augment or improve bone strength or shape. However, most bone grafts are found to be osteoconductive which is defined as the ability of a bone graft to facilitate the in growth of host bone into the bone graft material. This invention outlines a method and composition to not only promote osteoinduction but also prevent graft resorption by stimulating the production of osteoblasts and inhibiting osteoclast activity, and phagocytosis thereby resulting in an increase in net bone formation with greater density and volume.

The unfortunate removal of a tooth presents unique challenges in addition to grafting bone in other area of the body. The loss of a tooth precipitates loss of alveolar bone due the trauma of extraction and to exposure of alveolar bone to the oral environment. One of the greatest threats to the patient is osteomyelitis. Consequentially the body has developed a potent inflammatory response to exposure of bone in order to protect the patient from infection. Upon exposure of bone, a significant resorptive response occurs in order to resorb the exposed calcified tissue to prevent osteomyelitis. As the calcified portion of the exposed bone is being removed the body rushes to cover the exposed bone with soft connective tissue and ultimately epithelium to ward against infection. This process continues resulting in a loss of portions of the alveolar bone and often complete loss of the buccal wall of the extraction socket. After the initial healing of the extraction site the alveolar ridge gradually resorbs resulting in loss of functional support for dental implants and restorative appliances.

Esthetic compromises resulting from loss of the alveolus is often due to an unacceptable relationship of the alveolar ridge to prosthetic appliances. If a number of adjacent teeth are lost, facial deformity often occurs as a result of lack of support for the patients' lips and facial profile.

PRIOR ART

Fluoride is a drug which can clearly stimulate new bone formation and thus is capable of restoring lost bone in the spine (Pak et al., J. Clin. Endo. Metab., Vol 68:150-159, 1989). However, in a recent trial which included a placebo group, sodium fluoride in a immediate-release form at a high dosage of 75 mg/day with calcium carbonate over 4 years failed to reduce spinal fractures, even though bone density increased by 35% (Riggs et al., New Engl. J. Med., Vol 322:802-809, 1990).

In two prior patents (U.S. Pat. No. 4,726,952 and U.S. Pat. No. 4,888,182, both incorporated by reference herein), treated osteoporotic patients with sodium fluoride in a slow release tablet formulation that was shown to keep blood fluoride within safe and effective levels ("therapeutic window") and provide safety of usage (Pak et al., J. Bone Miner. Res., Vol 1:563-571, 1986). Unlike the immediate release sodium fluoride used by others, the slow release sodium fluoride caused minor and infrequent undesired side effects. When used with calcium citrate, spinal bone mass rose and the rate of spinal fractures decreased (as compared to the rate before treatment) (Pak et al., J. Clin. Endo. Metab., Vol 68:150-159, 1989). However other studies found that slow release fluoride did not reduce the fracture rate in osteoporosis patients. It was found that while fluoride increased bone mass it does not replace trabecula and for this reason fluoride has been shown to have little value in treating osteoporosis and reducing fractures.

U.S. Pat. No. 6,224,635 teaches Sodium Fluoride as an accelerator/stabilizer for Calcium sulfate used to coat dental implants.

Staboltz[11] and Nishino[12] both found that adding fluoride to bone graft material improved bone density by 20%.

Due to fluoride's ability to stimulate osteoblasts U.S. Pat. No. 3,287,219 discloses the oral administration of sodium fluoride to promote bone healing after bone fractures due to fluoride's ability to stimulate osteoblasts. However, oral supplementation of fluoride has never been proposed for improving the results of bone graft surgery. No prior art teaches the use of vitamin K for use in bone grafts. No prior art teaches the combination of fluoride and vitamin K for stimulating bone growth or for use in improving bone grafts.

BACKGROUND OF THE INVENTION

Bone growth has been a goal of bone graft surgery for since the early 1900's. Many bone graft materials have been designed in an effort to restore the skeleton to normal form and function. Recently bone graft surgery has been attempted to reshape bone in an effort to improve esthetics. The design of bone graft materials has focused on providing a bone graft material that would stimulate the host to regenerate lost bone or actually replace the lost bone with a synthetic substitute. Many bone graft surgeries use autografts taking bone form one part of the body to be used in another part of the same patient. Other bone graft surgeries use allografts using bone from another member of the same species most often harvested form cadavers. Zenografts are composed of hard tissue from another species such as coral or cow bone. Recent years have seen the development of synthetic bone graft materials most of which are composed of calcium phosphate based compounds designed to fill the bony defect. Synthetic bone grafts are designed to permit the body of the host to grow into the graft site and encompass the synthetic bone graft material or resorb the synthetic bone graft material and replace the bone graft with host bone. The ideal bone graft material would not have to be harvested from another site and would stimulate host bone formation to repair the defect. This invention embodies a bone graft material that stimulates osteoblasts and inhibits osteoclasts resulting in a net increase in bone over other current methods.

Over the years various methods and materials have been devised to limit the amount of alveolar bone lost after a tooth is removed. However, all of these methods have required a surgical procedure where incisions are made and a flap is raised to release the surrounding gingiva in order to cover the socket and bone graft. The procedure required a barrier be placed over the graft but under the gingiva to contain the bone graft that filled the socket. The procedure required the use of a bone graft material, subgingival barriers and a surgical procedure to place the material. This invention introduces a novel method that requires no surgical procedure other than tooth removal. The surrounding gingiva and underlying alveolar bone is undisturbed and a subgingival barrier is not required.

SUMMARY OF THE INVENTION

This invention presents a novel chemical composition of matter that stimulates osteoblast formation and inhibits osteoclastic and phagocytosis activity thereby resulting in a significant increase in bone formation. The novel combination of fluoride to stimulate osteoblasts and vitamin K to stimulate osteoblasts, inhibit osteoclasts, macrophages and polymorphonuclear leukocytes and initiate blood coagulation can be delivered in either the liquid or a powder depending on the application.

When extraction sockets are treated the method is to rinse the graft site with the invented chemical composition that will inhibit osteoclastic activity, macrophages, polymorphonuclear leukocytes and stimulate osteoblastic activity of the host bone. The chemical composition is also used as a wetting agent that is applied to the graft material prior to the placement of the graft material. The chemical composition resides in solution providing adhesion of the bone graft material helping to carry the graft material to the graft site. The chemical composition in free solution is immediately available for the stimulation of host bone. In addition to stimulating bone growth the chemical composition inhibits bone resorption and promotes blood coagulation.

All surgeries are traumatic to the host bone and result in initial bone resorption before bone growth can take over. The chemical composition in this invention is not only designed to stimulate bone formation but also is designed to inhibit bone resorption. As in all surgery proper placement of the bone graft requires control of bleeding to keep the graft material in place. The chemical composition in this invention is designed to stimulate bone formation, inhibit bone resorption and facilitate blood clot formation thereby preventing washing out of the graft material.

This invention presents in part novel packaging that permits precise compounding of the chemical composition of matter, efficient handling of the material in the operatory and ease of application. The method of application in extraction sockets does not require a surgical procedure due to the characteristics of the chemical composition of matter and the novel use of a supragingival barrier.

This invention includes unique packaging, composition, preparation and method of application making bone grafting of the post extraction socket simple and economical. This chemical composition of matter can be used to increase bone graft success in any osseous defect in the body.

DETAILED DESCRIPTION OF THE INVENTION

The invention contains the novel combination of fluoride which is known to stimulate osteoblast cell activity and vitamin K which is known to stimulate osteoblasts activity, inhibit osteoclasts (multinucleated giant cells) in addition to inhibiting phagocytosis of the graft material by macrophages and inhibiting polymorphonuclear leukocytes. In studies on human bone the novel chemical composition of matter of fluoride and vitamin k shows a significant increase in bone mineralization. The chemical composition of matter is delivered in a water based liquid or as a combination of a water based liquid and a calcium phosphate and/or calcium sulfate based powder. Another embodiment of this invention is the method by which this chemical composition of matter is delivered to the mammal in need thereof.

A novel method of delivery is to perfuse the chemical composition of matter under pressure into bone thereby stimulating osteogenesis. Another novel method of delivery is non-surgical placement of the chemical composition of matter in an extraction socket using a supragingival barrier.

Another embodiment of this invention is novel packaging and preparation of the chemical composition of matter permitting precise and simple preparation of the chemical composition of matter prior to use.

Fluoride is a ubiquitous element having many biological functions. The human body stores fluoride in the bones as a reservoir and releases the stored fluoride in an effort to maintain adequate fluoride for physiologic needs. Fluoride also incorporates into many molecules of the body replacing the hydroxyl radical thereby significantly increasing the biological activity of the molecule. The known functions of fluoride in the body are as follows:
Prevention of tooth decay (caries)[1]
Stimulation of cells that produce bone (osteoblasts)[2,3]
Increases production of antibodies[4]
Antibacterial[5]
Causes death (apoptosis) of cancer cells[6,7]
Prevents chromosome damage preventing mutation[8]
Increases bone volume and bone density[9,10]
Increases bone and bone density in bone grafts[11,12]
As fluoride intake increases cancer incidence decreases significantly[13]
As fluoride intake increases heart disease incidence decreases[14]

While vitamin K has never been applied to bone grafts its activities in bone are becoming more understood with recent research. Vitamin K is a critical ingredient in the formation and maintenance of bone. Vitamin K is one of the most important exogenous compounds that affect normal bone physiology. The known functions of vitamin k in the body as related to bone formation and maintenance are as follows.
Vitamin K stimulates osteoblastogenesis and inhibits osteoclastogenesis in human bone marrow cell culture.[15]
Vitamin K enhances osteocalcin accumulation in the extracellular matrix of human osteoblasts in vitro.[16]
Vitamin K inhibits adipogenesis, osteoclastogenesis, and ODF/RANK ligand expression in murine bone marrow cell cultures.[17]
Vitamin K inhibits prostaglandin synthesis in cultured human osteoblast-like periosteal cells by inhibiting prostaglandin H synthase activity.[18]
Vitamin K inhibits macrophage activity.[19]
Vitamin K inhibits of phagocytosis[20]

The ideal bone graft is resorbed quickly and replaced with bone that has a maximum amount of calcified tissue to support the loads placed on the newly regenerated bone. Another critical factor for a successful bone graft is that portions of the graft are not resorbed prior to converting the graft into new bone thereby losing volume. The most common problem with bone grafts are shrinkage of the grafted material as of result of resorption of the bone graft material. Shrinkage of the bone graft prior to being converted into bone is a result of osteoclastic activity and phagocytosis. For this reason the ideal bone graft must inhibit phagocytosis and osteoclastic resorption until osteogenesis can occur. Any bone graft material that is resorbed by phagocytosis or osteoclastic activity cannot be converted by osteoblasts into new bone.

The essential ingredient of an ideal bone graft material is a firm material that is biologically compatible with the surrounding tissues. The graft material must contain ingredients that stimulate osteogenesis in a physiological environment. The graft must contain compounds that inhibit osteoclasts and phagocytosis in a physiologic environment. This invention combines a novel combination of ingredients that meets the criteria for an ideal bone graft material and produces bone containing 90% mineralized tissue with minimal shrinkage of the grafted site.

Studies have established fluorides ability to stimulate osteogenesis and two studies have indicated an increase bone density. However fluoride alone only stimulates a small increase in bone density of 20%. The use of fluoride alone only stimulates osteoblasts while much of the graft material is resorbed prior to bone formation because osteoclastic activity and phagocytosis occurs prior to the arrival of osteoblasts resulting in shrinkage of the bone graft. The novel addition of vitamin K results in the stimulation of osteoblasts, inhibition of osteoclasts, macrophages and polynuclear leukocytes preventing the resorption and rejection of the bone graft thereby resulting in maintenance of the bone graft material and bone graft volume during osteogenesis.

Osteogenesis occurs in a very narrow range of pH. A pH above 7.4 and below 7.0 is known to inhibit osteogenesis.

A common bone graft material that has been in use for decades is calcium sulfate. When calcium sulfate is prepared with water prior to insertion into a bony defect the pH of the material is near a pH of 7. While calcium sulfate is well tolerated by the body it does not produce a significant increase of bone density and bone volume over controls. Our studies have found calcium sulfate not only produces mediocre results but often results in post operative pain. Our studies have found that while calcium sulfate mixed with water has a pH of 7, however, when calcium sulfate is inserted into a bony defect it mixes with the ubiquitous phosphate compounds found in the blood and bone and the pH drops to a pH of 5.9. This factor is responsible for bone graft material containing calcium sulfate having mediocre regenerative abilities and often result in post operative pain. The reaction of calcium sulfate in the body is represented by the following reaction.

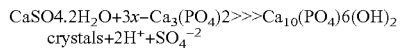

$$CaSO4.2H_2O+3x-Ca_3(PO_4)2>>>Ca_{10}(PO_4)6(OH)_2 \text{ crystals}+2H^++SO_4^{-2}$$

In order to optimize the physiologic environment and maintain a pH of 7.2 that is ideal of osteogenesis this invention introduces a novel use of a buffer when calcium sulfate is used as a carrying medium for the chemical composition of matter. One embodiment of this invention is the addition of fluoride, vitamin K and sodium bicarbonate to a liquid of water and a powder of calcium phosphate and/or calcium sulfate in ideal concentrations for optimum osteogenesis. As stated earlier the addition of calcium sulfate to host tissues or to calcium phosphate in the graft material results in a local pH of 5.9 as is reflected in the following formula.

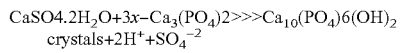

$$CaSO4.2H_2O+3x-Ca_3(PO_4)2>>>Ca_{10}(PO_4)6(OH)_2 \text{ crystals}+2H^++SO_4^{-2}$$

The addition of sodium bicarbonate or other comparable buffers produces the following reaction.

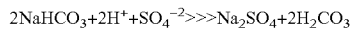

$$2NaHCO_3+2H^++SO_4^{-2}>>>Na_2SO_4+2H_2CO_3$$

Buffering the reaction of calcium sulfate with sodium bicarbonate in the proper concentration produces an ideal pH for osteogenesis.

The novel chemical composition of matter of fluoride and vitamin K in a carrier of water, calcium sulfate powder and calcium phosphate powder buffered by sodium bicarbonate was evaluated for effectiveness in extraction sockets. Six extraction sockets were treated with the novel chemical composition of matter and six untreated sockets served as controls. Core samples were taken after a minimum of three months post extraction. After a minimum healing period of 3 months an 8 mm by 2 mm core sample was taken using a trephine in an electric motor. The samples that were taken from molar sites were taken from areas confirmed to be from previous root sites and not from previous interradicular areas. This was confirmed clinically and radiographically during surgery. The core samples were demineralized and stained with H and E. The 8 mm core samples were marked at 2 and 6 mms to clearly identify the 4 mm central portion of the core samples. Only the central 4 mm of the core sample was evaluated for percent of mineralized tissue. This excluded any cortical plate and the artifacts created at the end of the core sample. All samples were evaluated blinded and scored for percent of mineralization by multiple investigators with the scores averaged. Mineralized tissue was identified with no effort to distinguish between types of bone. The control sites that received no graft treatment resulted in an average of 27% mineralized tissue. The test sites that received the novel chemical composition of matter averaged 90% mineralized tissue. The difference between test and control samples were significant $p=<0.05$.

Exposure of bone during surgery is known to result in resorption of bone during healing. When a tooth is extracted bone is always exposited in the extraction socket. If the socket is left untreated an inflammatory infiltrate fills the socket to ward off infection. During this process bone is resorbed that lines the socket prior to the socket filling with bone. If not only the socket bone is exposed during tooth extraction but also the buccal and lingual bone of the alveolus, extensive resorption of the alveolar bone can occur resulting in esthetic and functional deficiencies.

Socket preservation procedures have been developed to treat the extraction socket. The common method requires the buccal and lingual flaps to be lifted off the alveolus in the area of the extraction socket and the flaps are released and elevated over the extraction socket to achieve primary closure over the graft material that is placed in the extraction socket. The elevation of the flaps facilitates bone growth in the extraction socket but results in increased resorption of the buccal and lingual bone due to exposure during surgery.

An embodiment of this invention is a method of packaging and placing the chemical composition of matter without raising gingival flaps that result in buccal and lingual bone resorption. An embodiment of this invention for regenerating sockets is the composition of fluoride, vitamin k, sodium bicarbonate, calcium sulfate and calcium phosphate and water. A precise amount of liquid is injected into the pouch. Upon mixing the water and powder will remain in a paste consistency in the sterile packet until opened. In order to ensure precise measurement and concentration of the chemical composition of matter a precise amount of liquid is drawn into a sterile syringe. The precise amount of liquid is injected into a packet containing the powder. Shaking down the liquid ensures proper distribution of the liquid into the powder. The packet can then be left until needed by the operator. This feature permits precise preparation of the graft material prior to the beginning of surgery. Only when the pouch is opened and exposed to air will the graft material begin to crystallize.

After the tooth is removed and the socket is debrieded, the socket is then irrigated with the liquid and allowed to set as the fluoride anions incorporate into the socket wall. The socket is then evacuated and the graft is placed into the socket and absorbable gauze is placed on the graft to initiate crystallization. After the graft has reached a firm consistency a supragingival barrier is placed over the graft and fixed is place by adhesion, sutures or packing material. The supragingival barrier retains the graft material and facilitates connective tissue covering of the graft followed by a covering of epithelium. This embodiment of the invention provides for a precise concentration of the graft components for optimum osteogenesis. This embodiment of the invention also provides for an economical and efficient method delivering the chemical composition of matter to the patient in need thereof. This embodiment avoids flap surgery thereby reducing pain and morbidity and prevents bone resorption of the buccal and lingual wall of the alveolus. The combination of this method and the chemical composition of matter results in a 63% increase in bone density over controls.

In this embodiment the novel chemical composition of matter is supplied in a liquid base of water and a powder base of calcium phosphate and/or calcium sulfate and sodium bicarbonate. The liquid is drawn into a sterile syringe. The graft material is contained in a sterile flexible packet.

Exact compounding to provide precise concentration of the active ingredients is achieved by specifying the exact amount of liquid per sterile flexible packet.

After the addition of the precise amount of liquid the chemical composition of matter can now be set aside until needed by the operator. Setting will not begin until the packet is opened. When the operator is ready to insert the graft material the packet is cut open to access the precisely mixed material. With precise measurement an easily controlled paste is ready for the graft site. The socket is filled with the graft material.

The supragingival barrier is cut into the proper shape and prepared for placement over the extraction site. The supragingival barrier is placed directly over the extraction socket and exposed graft material.

The supragingival barrier is held in place by sutures or packing material. When the supragingival barrier is sutured in place the edges of the barrier are folded over the sutures to lock it in place. Treatment is complete with no need for gingival flap surgery or subgingival barriers. The barrier is removed in two weeks.

The most challenging aspect of bone regeneration is appositional bone growth. Appositional bone growth is the growing of bone on the surface of bone. Bone grafts placed on the surface of bone are often quickly resorbed because the resorptive cells arrive more readily than the regenerative cells and consequentially the bone graft is reduced in size prior to being converted into host bone. The use of the novel chemical composition of matter the success of appositional bone grafts are significantly increased. Due to stimulation of osteoblasts and inhibition of resorption of the graft material bone can be increased in height and width as appositional bone growth is achieved.

One embodiment of this invention is the combination of fluoride, vitamin K and sodium bicarbonate in a liquid of water and a powder of calcium sulfate and/or calcium phosphate. Another embodiment of this invention is the combination of fluoride, vitamin K in a liquid and a powder of calcium sulfate, sodium bicarbonate and/or calcium phosphate. Another embodiment of this invention is the combination of fluoride, in a liquid of water and a powder of vitamin k, calcium sulfate, sodium bicarbonate and/or calcium phosphate. Another embodiment of this invention is water and a powder of fluoride, vitamin k, calcium sulfate, sodium bicarbonate and/or calcium phosphate. Another embodiment of this invention is the combination of fluoride and vitamin K in a liquid of water.

Bone density is a major medical concern. Areas of osteoporosis are susceptible to increased fracture rates due to a decrease in mineralized tissue. One embodiment of this invention is designed to treat localized areas of bone to increase osteogenesis and inhibit osteoclastic activity thereby increasing bone density. A perforation is made in the cortical plate of bone and the chemical composition is injected under pressure to stimulate osteogenesis in the surrounding bone. This method is applicable to any bone in the body in need of increased bone density but is also ideal for implant placement. When an implant site in prepared in bone the bony socket that is to receive the implant is filled with this embodiment of the invention. As the implant is driven to place the chemical composition of matter is forced under pressure throughout the surrounding tissue resulting in increased osteogenesis and a decrease in osteoclastic activity resulting in increased bone density with improved integration and stability of the implant.

The novel chemical composition of matter is drawn into a sterile syringe. The novel chemical composition of matter fills the infusion site. As the implant is seated infusion occurs into the surrounding bone stimulating bone formation with increased density and improved integration.

The novel chemical composition of matter can be infused under pressure into any bone in need of increased mineralized density.

Upon contact with the patient's bone, soluble fluoride will immediately initiate osteoblastic cell production in the surrounding bone. Bone mass is a result of the balance between bone formation and bone resorption. This invention not only stimulates bone formation but also inhibits bone resorption resulting in a further net increase in bone mass. While the primary purpose of vitamin k in this invention is to prevent bone resorption and stimulate osteoblasts another use of vitamin K in this invention is to produce blood coagulation at the surgical site. It is important to control bleeding in the surgical site in order to prevent the bone graft from being washed out of the graft site resulting in failure of the bone graft surgery.

Osteoblasts have traditionally been thought to be present only in bone. However, recent finding confirm a significant number of osteoblast progenitor cells present in circulating blood.[21] The number of circulating osteoblast progenitor cells found in the blood increases during time of bone growth such as puberty and as a response to bone injury. Another embodiment is the administration of fluoride and/or vitamin K prior, during and post bone graft surgery in order to increase the number of circulating osteoblast progenitor cells. By increasing circulating progenitor cells an increase in osteoblasts arriving at the graft site will increase and accelerate the process of osteogenesis. Prior to these findings osteoblasts were thought to migrate into the graft site from adjacent periosteal and bone. Stimulation of osteoblast circulating in the blood will improve the success of bone graft surgery.

REFERENCES

1 American Dental Association http://www.ada.org/public/topics/fluoride
2 Briancon D, Meunier P J, 1981 Treatment of osteoporosis with fluoride, calcium, vitamin D. Orthop Clin North Am 12:629-648.
3 Harrison J E, McNiell K G et al 1981 Three-year changes in bone mineral mass of osteoporotic patients based on neutron activation analysis of the central third of the skeleton. J Clin Endocrinol Metab 52:751-758.
4 Butler J E, Satam M, Ekstrand J. Fluoride: an adjuvant for mucosal and systemic immunity. Immunol Lett. 1990 December; 26(3):217-20.
5 Mangi S L, Summer W A, Phillips R W, Swartz M L. Antibacterial action of certain fluoride-containing dental restorative materials. J Dent Res. 1959 January-February; 38(1):88-95.
6 Hirano S, Ando M. Fluoride mediates apoptosis in osteosarcoma UMR 106 and its cytotoxicity depends on the pH. Arch Toxicol 1997; 72(1):52-8.
7 Anuradha C D, Kanno S, Hirano S. Fluoride induces apoptosis by caspase-3 activation in human leukemia HL-60 cells. Arch Toxicol 2000; 74(4-5):52-8.

8 Vogel E. Strong antimutigenic effects of fluoride on mutation induction by trenimon and 1-phenyl-3,3-dimethyltriazene in *Drosophila Melanogaster*. Mutation Research 1973; 20:339-352.

9 Pak CY, Sakhaee K, Adams-Huet B, Piziak V, Peterson R D, Poindexter J R. Treatment of postmenopausal osteoporosis with slow-release sodium fluoride. Final report of a randomized controlled trial. Am Intern Med. 1995 Sep. 15; 123(6):401-8.

10 Reginster J Y, Meurmans L, Zegels B, Rovati L C, Minne H W, Giacovelli G, Taquet A N, Setnikar I, Collette J, Gosset C. The effect of sodium monofluorophosphate plus calcium on vertebral fracture rate in postmenopausal women with moderate osteoporosis. A randomized, controlled trial. Ann Intern Med. 1998 Jul. 1; 129(1):1-8.

11 Stabholz A, Brayer L, Gedalia I, Yosipovitch Z, Soskolne W A. Effect of fluoride on autogenous iliac cancellous bone grafts and marrow transplants in surgically created intrabony defects in dogs. J. Periodontol. 1977 July; 48(7): 413-7.

12 Nishino T. Nippon Seikeigeka Gakkai Zasshi. Experimental study on hydroxyapatite soaked in sodium fluoride—with special reference to bone formation. 1991 December; 65(12):1199-1210.

13 Steiner G G. Cancer incidence rates and environmental factors: An ecological study. Journal of Environmental Pathology, Toxicology and Oncology 2002; 21(3):205-212.

14 Recent study conducted in Finland not yet published.

Koshihara Y, Hoshi K, Okawara R, Ishibashi H, Yamamoto S. Vitamin K stimulates osteoblastogenesis and inhibits osteoclastogenesis in human bone marrow cell culture. J. Endocrinol. 2003 March; 176(3):339-48.

16 Koshihara Y, Hoshi K. Vitamin K2 enhances osteocalcin accumulation in the extracellular matrix of human osteoblasts in vitro. J Bone Miner Res. 1997 March; 12(3):431-8.

17 Takeuchi Y, Suzawa M, Fukumoto S, Fujita T. Vitamin K(2) inhibits adipogenesis, osteoclastogenesis, and ODF/RANK ligand expression in murine bone marrow cell cultures. Bone. 2000 December; 27(6):769-76.

18 Koshihara Y, Hoshi K, Shiraki M. Vitamin K2 (menatetrenone) inhibits prostaglandin synthesis in cultured human osteoblast-like periosteal cells by inhibiting prostaglandin H synthase activity. Biochem Pharmacol. 1993 Oct. 19; 46(8):1355-62.

19 Yakamoto W, Isomura H, Fujie K, Iizuka T, Nishihira J, Tatebe G, Takahashi K, Osaki Y, Komai M, Tamai H. The effect of vitamin K2 on bone metabolism in aged female rats. Osteoporos Int. 2005 Apr. 22

20 Koyano H, Someya A, Nagaoka I, Yamashita T. Effect of vitamin K3 on macrophage functions and intracellular calcium. Comp Biochem Physiol A. 1988; 91(1):115-21

21 Eghbali-Fatourechi G Z, Lamsam J, Fraser D, Nagel D, Riggs B L, Khosla S. Circulating osteoblast-lineage cells in humans. N Engl J. Med. 2005 May 12; 352(19):2014-6.

The invention claimed is:

1. A method for promoting bone growth, inhibiting bone resorption prior to the replacement of a bone graft with host bone, and facilitating blood clot formation following bone graft surgery, comprising the step of administering a therapeutic amount of vitamin K directly to the area of bone to be treated in a bone graft site during bone graft surgery, the vitamin K being included as a component in bone graft composition and having a composition sufficiently solid to maintain volume during bone growth at the bone graft site.

2. The method of claim 1, further including the step of applying bone graft material to the area of bone to be treated, wherein the bone graft material comprises water, calcium sulfate and sodium bicarbonate.

3. The method of claim 1, further including the step of applying bone graft material to the area of bone to be treated, wherein the bone graft material comprises water, calcium sulfate and sodium bicarbonate and calcium phosphate.

4. The method of claim 1, further including the step of applying bone graft material to the area of bone to be treated, wherein the bone graft material is any physiologically acceptable bone graft material.

5. The method of claim 1, further including the step of administering a therapeutic amount of fluoride in combination with the administration of a therapeutic amount of vitamin K.

6. The method of claim 5, wherein the vitamin K and the fluoride are mixed with bone graft material and the bone graft material is thereafter applied to the area of bone to be treated.

7. The method of claim 6, wherein vitamin K and fluoride are administered to the bone graft site in liquid form prior to placement of bone graft material.

8. The method of claim 5, wherein vitamin K and fluoride are administered to the bone graft site in liquid form prior to placement of bone graft material.

9. The method of claim 5, wherein the vitamin K is mixed with bone graft material and the bone graft material is thereafter applied to the area of bone to be treated.

10. The method of claim 9, wherein the vitamin K is administered to the bone graft site in liquid form prior to placement of bone graft material.

\* \* \* \* \*